US008539980B2

(12) United States Patent
Tanner et al.

(10) Patent No.: US 8,539,980 B2
(45) Date of Patent: *Sep. 24, 2013

(54) DEVICE FOR CONTROLLED OPERATION OF A SURGICAL OR DENTAL DRIVE UNIT

(75) Inventors: Peter Tanner, Bubendorf (CH); Arthur Meili, Thurnen (CH)

(73) Assignee: Depuy Synthes Products, LLC, Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/568,596

(22) Filed: Aug. 7, 2012

(65) Prior Publication Data

US 2012/0329007 A1   Dec. 27, 2012

Related U.S. Application Data

(63) Continuation of application No. 11/915,263, filed as application No. PCT/CH2005/000294 on May 25, 2005, now Pat. No. 8,256,460.

(51) Int. Cl.
*E03B 1/00* (2006.01)
*F16K 31/06* (2006.01)

(52) U.S. Cl.
USPC ........ 137/614.19; 251/89; 251/111; 251/295; 433/84; 173/169

(58) Field of Classification Search
USPC ................ 137/613, 614.19; 251/89, 95, 111, 251/295, 252, 255, 258, 251; 239/526, 583; 604/128; 433/80, 84, 85, 133; 409/904; 200/86.5; 318/551; 173/168, 169, 170; 222/153.13–135.14, 153.11, 402.15, 179

See application file for complete search history.

(56) References Cited

U.S. PATENT DOCUMENTS

| 3,752,241 | A  | * | 8/1973  | Bent ............................. 173/221 |
| 4,106,750 | A  | * | 8/1978  | Karden et al. ................ 251/282 |
| 4,666,124 | A  | * | 5/1987  | Giacobbi ........................ 251/56 |
| 5,435,339 | A  | * | 7/1995  | Hayes ...................... 137/315.04 |
| 5,569,256 | A  | * | 10/1996 | Vaughn et al. .................. 606/80 |
| 6,032,922 | A  | * | 3/2000  | Shew ............................... 251/99 |
| 6,176,853 | B1 | * | 1/2001  | Stolyarenko ..................... 606/1 |
| 6,520,976 | B1 | * | 2/2003  | Gage ............................. 606/170 |

* cited by examiner

*Primary Examiner* — Stephen M Hepperle
*Assistant Examiner* — Seth Faulb
(74) *Attorney, Agent, or Firm* — Fay Kaplun & Marcin, LLP

(57) ABSTRACT

A device for operation of a surgical or dental drive unit includes a control valve attached to a drive unit to control a flow rate of a compressed fluid flowing from a compressed fluid source to the drive unit. The control valve includes (a) a first control arrangement controlling a rate of flow of the compressed fluid through the control valve; (b) a control switch; and (c) a control sleeve controlled by the control switch to axially move along a longitudinal axis of the drive unit between a first configuration in which the control valve is locked and closed to fluid flow and a second configuration in which the control valve is unlocked and the first control arrangement controls the rate of flow therethrough.

18 Claims, 3 Drawing Sheets

DEVICE FOR CONTROLLED OPERATION OF A SURGICAL OR DENTAL DRIVE UNIT

Figure 1:
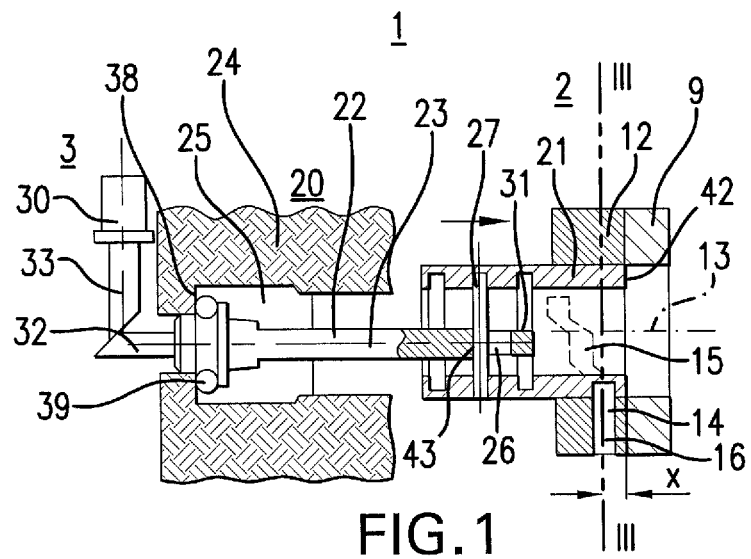

This application is a Continuation of U.S patent application Ser No. 11/915,263 Mar. 24, 2008, now U.S. Pat. No. 8,256,460, which is a 371 application of PCT Application Serial No. PCT/CH2005/000294 filed May 25, 2005. The Specifications of both applications/patent are incorporated herewith by reference.

The invention relates to a device for controlled operation of a surgical or dental drive unit according to the concept of claim 1.

From U.S. Pat. No. 3,989,952 HOHMANN a dental apparatus is known which is provided with a plurality of instruments and electrically or pneumatically driven drive devices. Each drive device may be actuated by means of a foot controlled arrangement or alternatively by a hand controlled means. Furthermore, the dental apparatus has a support arrangement for the drive devices, so that upon withdrawal of a drive device from its support a switch is closed thus permitting actuation of the drive device. Once the drive device is withdrawn from its support it may be erroneously or unintentionally actuated.

On this point, the invention intends to provide remedial measures. The invention is based on the objective of providing a device for controlled operation of a drive device that has an integrated main switch by means of which the drive is either put out of operation and locked or else a selection between an integrated first control means or a remote second control means is permitted.

The invention solves the posed problem with a device for controlled operation of a surgical or dental drive unit that displays the features of claim 1.

The advantages achieved by the invention are essentially to be seen in the fact that, thanks to the device according to the invention the operator may choose between an actuation of the drive unit by means of a first control means controlled by hand or a second control means controlled by hand, foot or by means of a computer;

the operator does not have to avert his attention from the operating site since the control switch is attachable to the drive unit; and a secure operation is permitted since the control valve may be locked in its closed position thereby preventing an erroneous or unintended actuation of the drive unit.

In a preferred embodiment the control switch has a fourth position D in which the control valve may only be partially opened. This allows a restriction of the flow rate through the control valve to an allowable flow rate "r" which is smaller than the maximum flow rate "R". The restriction of the flow rate allows a limitation of the maximum rotational speed of the drive unit with regard to the chosen tool, e.g. drill bits with different diameters.

Preferably, the allowable flow rate "r" is in the range of 25% and 75% of the maximum flow rate "R".

In a further embodiment the control switch is configured to permit a continuous variation of the ratio r/R, therewith allowing a continuous variation of the rotational speed of a drive unit coupled to the device.

In another embodiment the control switch is configured to permit a stepwise variation of the ratio r/R.

In yet another embodiment the first control means comprise an operating means which is reversibly attachable to the device. This embodiment allows the advantage that the operator is not disturbed through the hand controlled operating means when the control of the drive unit is performed through the second control means, e.g. a control means being operated by foot or by a computer.

In a further embodiment the operating means is provided with a locking means for being reversibly locked. This embodiment allows the advantage that a drive unit coupled to the device may not be unintendetly actuated when the device together with the drive unit is laid down.

In yet a further the second means is actuable by foot. This embodiment allows the advantage that the drive unit may be alternatively operated by hand by means of the first control means when the control switch is in position B or by foot by means of the second control means when the control switch is in position C.

In another embodiment the control valve is open but put out of operation upon switching the control switch in its position C. This allows that advantage that the drive unit may be operated by means of a common control means actuated by foot.

In a further embodiment the control valve is provided with a valve body having a longitudinal axis, a control sleeve apt to lock or unlock the control valve and a valve piston being apt for the control of the flow rate of a compressed fluid.

In yet a further embodiment the valve piston is displaceable along the longitudinal axis by means of the first control means in order to control the flow rate of compressed fluid.

The invention and additional configurations of the invention are explained in even more detail with reference to the partially schematic illustration of several embodiments.

Figure 2:
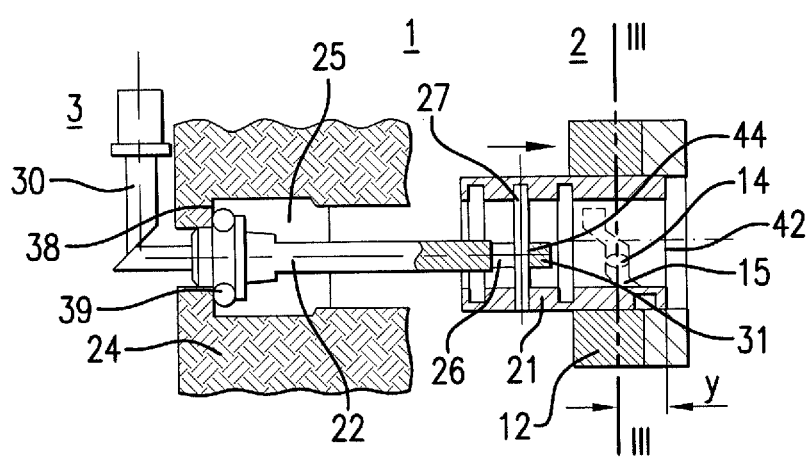
Figure 3:
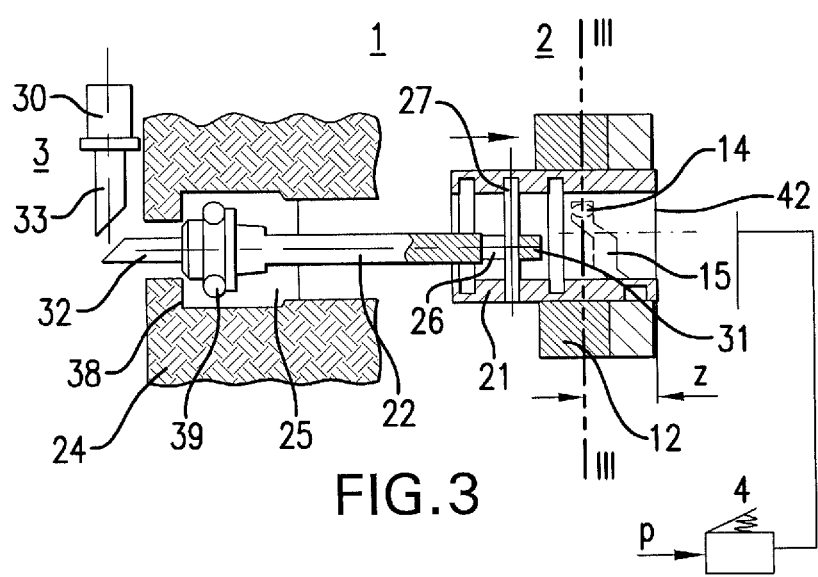
Figure 4:
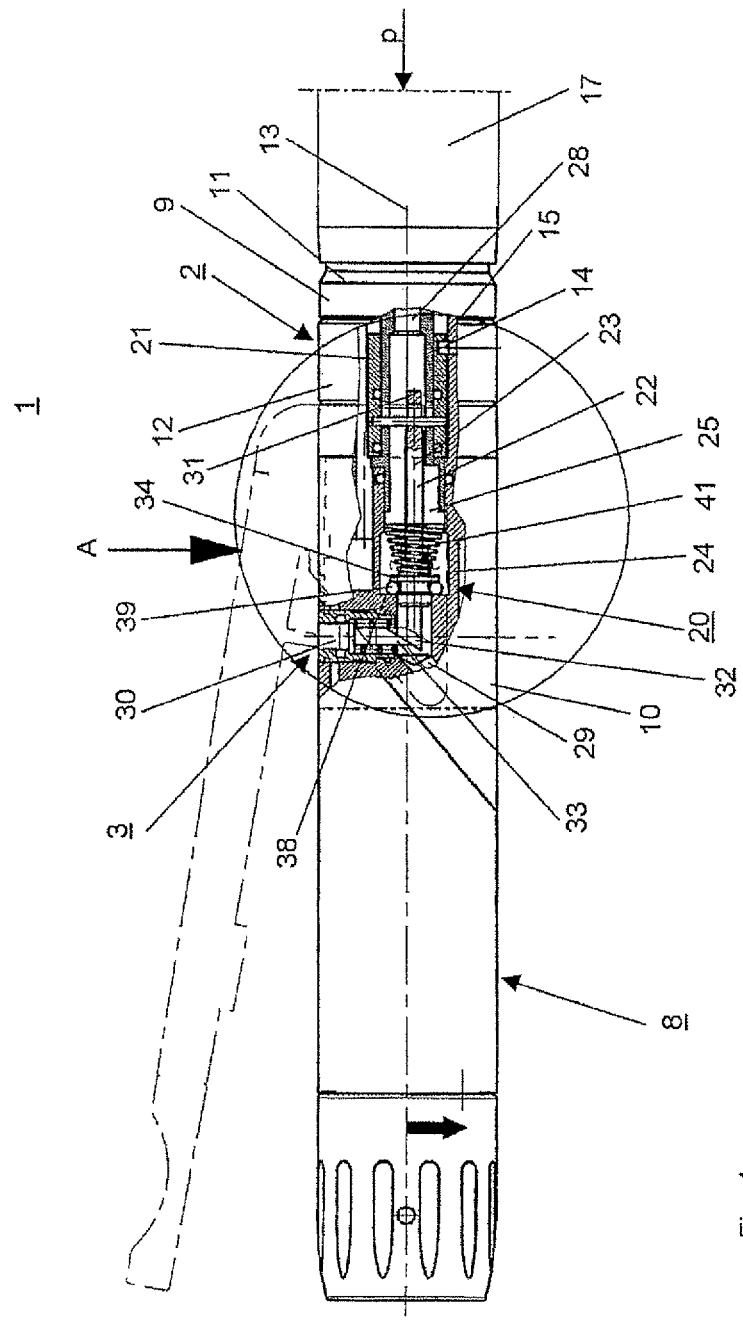
Figure 5:
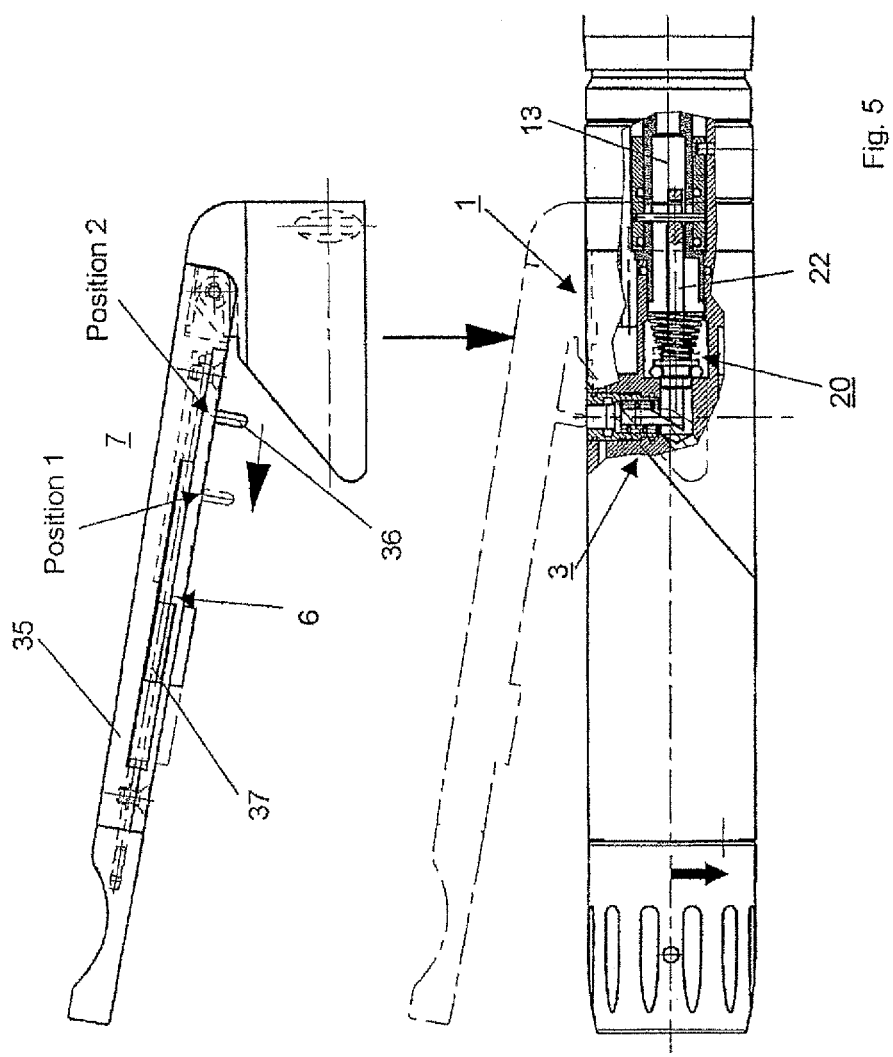

The figures depict:

FIG. 1 a schematic view of an embodiment of the control valve according to the invention in its closed and locked position;

FIG. 2 a schematic view of the embodiment of the control valve shown in FIG. 1 in its unlocked position and being controllable by the first control means actuable by hand;

FIG. 3 a schematic view of the embodiment of the control valve shown in FIGS. 1 and 2 in its unlocked position and being controllable by means of a second control means actuated by foot;

FIG. 4 a longitudinal section through a drive unit with an integrated embodiment of the device according to the invention; and FIG. 5 a plane view of an embodiment of the device with an operating means for the first control means actuable by hand and having integrated locking means in the unlocked state.

FIGS. 1 to 3 schematically depict the control valve 20 with the ring member 12 of the control switch 2 (FIG. 4) being in position A (FIG. 1), in position B (FIG. 2) and in position C (FIG. 3). Upon rotating the ring member 12 around the central axis 13 of the device 1 (FIG. 4) the pin 14 slides along the peripheral axially stepped groove 15 at the control sleeve 21 while keeping its axial position on the line III-III such that the control sleeve 21 is axially displaced. The different axial positions of the control sleeve 21 permit firstly to lock (Position A) or unlock (Position B or C) the control valve 20. Therefore, the valve piston 22 comprises an oval aperture 26 arranged at its trailing end 31 and penetrating the valve piston 22 orthogonal to the longitudinal axis 23 of the valve piston 22. Furthermore, the control sleeve 21 is provided with a rod member 27 arranged diametrically and orthogonally to the longitudinal axis 23 of the valve piston 22 whereby the rod member 27 penetrates the oval aperture 26.

Upon switching the control switch 2 in its position A (FIG. 1) by axially displacing the control sleeve 21 to a distance x between the line III-III and the terminal end face 42 of the control sleeve 21 by means of rotating the ring member 12 the rod member 27 is also axially displaced until it contacts the wall of the oval aperture 26 at the first end 43 of the oval aperture 26 which is remote to the terminal end face 42. In this position of the control sleeve 21 the valve piston 22 is axially blocked. The oval aperture 26 is situated at the trailing end 31 of the valve piston 22 while the leading end 32 of the valve piston 22 is configured obliquely to the longitudinal axis 23, whereby said leading end 32 matches with the complementary oblique front piece 33 of the slide member 30.

Since in position A the valve piston 22 is locked against displacement towards the rod member 27 the control valve 20 may not be actuated through the slide member 30.

In FIG. 2 the control switch 2 is shown in its position B in which the control sleeve 21 with the rod member 27 is axially displaced to a distance y>x between the line III-III and the terminal end face 42 of the control sleeve 21. The rod member 27 is now in contact with the wall of the oval aperture 26 at the second end 44 of the oval aperture 26 which is next to the terminal end face 42 of the control sleeve 21. Such the valve piston 22 may now be displaced parallel to its longitudinal axis 23 towards the rod member 27 by means of the first control means 3 therewith continuously opening or closing the control valve 20 at the valve face 38.

FIG. 3 depicts the control switch 2 in its position C in which the control sleeve 21 with the rod member 27 is axially displaced to a distance z>y between the line III-III and the terminal end face 42 of the control sleeve 21. Since the rod member 27 is in contact with the wall at the second end 44 of the oval aperture 26 the valve piston 22 is axially displaced towards the rear end 11 of the device 1 (FIG. 4) and the control valve 20 is opened at the valve face 38. The valve piston 22 is situated so far away from the slide member 30 that the slide member 30 is at a distance to the leading end 32 of the valve piston 22 such that the valve piston 22 may not be axially displaced through the displacement of the slide member 30. The control of the flow of a compressed fluid must now be effected by means of a second control means 4, e.g. an external control valve operated by foot connected to the adapter 9 and to a source of compressed fluid p available in the operating room.

FIG. 4 depicts an embodiment of the device 1 which is coaxially attached to a drive unit 8 with its front end 10 and which is provided with an adapter 9 for a flexible tube 17 for compressed fluid at its rear end 11. The flexible tube 17 is connectable e.g. to a source of compressed fluid p available in the operating room. The control valve 20 comprises a valve housing 24 with a central cavity 25, an inlet 28 adjacent to the adapter 9 for the compressed fluid and an outlet 29 connected to the drive unit 8. Furthermore, the control valve 9 comprises a valve piston 22 being displaceable in the cavity 25 along its longitudinal axis 23 and relative to the valve housing 24. Towards the front end 10 of the device 1 the valve piston 22 comprises a shoulder 34 concentrically arranged and having a valve seal 39 attached. Upon deactuating the control valve 20 the valve seal 39 is axially pressed against a valve face 38 at the valve housing 24 by means of a helical spring 41. Adjacent to the shoulder 34 the leading end 32 of the valve piston 22 is located which is obliquely shaped relative to longitudinal axis 23 of the valve piston 22. The oblique shaped leading end 32 of the valve piston 22 permits an axial displacement of the valve piston 22 against the force of the spring 41 by means of a slide member 30 being slideable perpendicularly to the longitudinal axis 23 of the valve piston 22 and having a complementarily shaped oblique front piece 33. In FIG. 1 the control switch 2 is in its position A such that the control valve 20 is locked and closed.

The control switch 2 comprises a control sleeve 21 being displaceable parallel to the longitudinal axis 23 and by means of which the control valve 20 may be put in one of its positions A;B;C i.e. locked and closed, unlocked and having the flow rate controlled by means of the first control means 3, or unlocked and open. The actuation of the control switch 2 is effected through a ring member 12 being arranged concentrically to the central axis 13 of the device 1 and being rotatable around the central axis 13 thus switching between the positions A;B;C. Upon rotating the ring member 12 from one position to another the control sleeve 21 is axially displaced by means of a pin 14 connected to the ring member 12 and engaging a groove 15 in the control sleeve 21 which extends on the outer periphery of the control sleeve 21 and which is axially stepwise configured (not shown) therewith allowing to axially displace the control sleeve 21.

FIG. 5 depicts an embodiment of operating means 7 actuable by hand which permits control of the first control means 3. The operating means 7 is reversibly mountable to the device 1. The operating means 7 comprises as a lever 35 being pivotably attached. The lever 35 includes a tappet 36 by means of which the slide member 30 may be pushed towards the leading end 32 of the valve piston 22 upon pivoting the lever 35 towards the central axis 13 of the device 1. Subsequently, the valve piston 22 is axially displaced thus permitting the control of the flow rate of compressed fluid through the control valve 20. Furthermore, the lever 35 includes a locking means 6 realised through a slide switch 37 by means of which the tappet 36 is moveable along the lever 35 in a first position 1 in which it may not contact the slide member 30 and in a second position 2 in which the tappet 36 may actuate the slide member 30.

The invention claimed is:

1. A device for operation of a surgical or dental drive unit, comprising:
   a control valve attached to a drive unit to control a flow rate of a compressed fluid flowing from a compressed fluid source to the drive unit, the control valve including:
   a first control arrangement controlling a rate of flow of the compressed fluid through the control valve;
   a control switch; and
   a control sleeve controlled by the control switch to axially move along a longitudinal axis of the drive unit between a first configuration in which the control valve is locked and closed to fluid flow and a second configuration in which the control valve is unlocked and the first control arrangement controls the rate of flow therethrough.

2. The device of claim 1, wherein the drive unit comprises an adapter for connection of the drive unit to a tube having compressed fluid.

3. The device of claim 1, wherein the first control arrangement is connected to a first operating means configured and dimensioned for actuation by a hand of a user.

4. The device of claim 3, wherein the first operating means is a lever connected to an outer surface of the drive unit.

5. The device of claim 1, wherein the control switch further comprises a ring member having an opening housing a portion of the control sleeve therewithin, wherein rotation of the ring member about the longitudinal axis causes axial displacement of the control sleeve.

6. The device of claim 5, wherein the ring member is connected to a pin, wherein rotation of the ring member causes movement of the pin into an axially stepped groove provided in the control sleeve.

7. The device of claim 1, wherein the control valve further comprises a valve piston extending from a first end to a second end and displaceable along the longitudinal axis by the first control arrangement.

8. The device of claim 7, further comprising a valve housing having the valve piston positioned therein, wherein the first end of the valve piston comprises a shoulder having a valve seal attached thereto, the valve seal being axially pressed against a valve face of the valve housing by a spring.

9. The device of claim 1, further comprising a second control arrangement controlling a rate of flow of the compressed fluid through the control valve independently of the first control arrangement.

10. The device of claim 9, wherein the control sleeve is controlled by the control switch to move to a third configuration in which the control valve is unlocked and the second control arrangement controls the rate of flow therethrough.

11. The device of claim 10, wherein the second control arrangement is connected to a second operating means configured and dimensioned for actuation by a foot of the user.

12. A device for controlled operation of a surgical or dental drive unit which is driven by a compressed fluid source, comprising:
a control valve attachable to a drive unit for controlling a flow rate of a compressed fluid flowing from a compressed fluid source to the drive unit; and
a control sleeve axially displaceable along a longitudinal axis of the control valve, movement of the control sleeve moving the control valve between first, second and third positions, wherein in the first position, the control valve is locked and closed, in the second position, the control valve is unlocked and the flow rate of the compressed fluid is regulated by a first control arrangement, and in the third position, the control valve is unlocked and the flow rate of the compressed fluid is regulated by a second control arrangement.

13. The device of claim 12, wherein the control switch is movable to a fourth position in which the control valve is partially open to permit flow therethrough at a reduced rate smaller than a maximum flow rate.

14. The device of claim 12, further comprising a valve body housing a valve piston therein, the valve piston being displaceable along the longitudinal axis by the first control arrangement.

15. The device of claim 12, wherein axial movement of the control sleeve is controlled by a control switch.

16. The device of claim 15, wherein the control switch is controlled by a lever.

17. The device of claim 15, wherein the control switch further comprises a ring member having an opening housing a portion of the control sleeve therewithin, wherein rotation of the ring member about the longitudinal axis causes axial displacement of the control sleeve.

18. The device of claim 17, wherein the ring member is connected to a pin, wherein rotation of the ring member causes movement of the pin into an axially stepped groove provided in the control sleeve.

* * * * *